United States Patent [19]

Buonicore et al.

[11] Patent Number: 4,831,196
[45] Date of Patent: May 16, 1989

[54] PROCESS FOR OLEFIN OXIDE DETOXIFICATION

[75] Inventors: Anthony J. Buonicore, Fairfield; Pankaj R. Desai, Shelton, both of Conn.

[73] Assignee: Chemrox, Inc., Shelton, Conn.

[21] Appl. No.: 177,741

[22] Filed: Apr. 5, 1988

Related U.S. Application Data

[63] Continuation-in-part of Ser. No. 521,955, Aug. 10, 1983, abandoned, which is a continuation-in-part of Ser. No. 409,830, Aug. 20, 1982, abandoned.

[51] Int. Cl.$^4$ .................. C07C 29/00; C07C 31/20; C07C 17/38; C07C 19/08
[52] U.S. Cl. .................... 568/867; 549/542; 570/177; 570/179
[58] Field of Search ............. 549/542; 568/867; 570/177, 179

[56] References Cited

U.S. PATENT DOCUMENTS

| | | | |
|---|---|---|---|
| 1,641,710 | 9/1927 | Untiedt | 568/867 |
| 2,135,271 | 11/1938 | Balcar | 260/634 |
| 2,255,411 | 9/1941 | Cohen et al. | 568/867 |
| 2,325,577 | 7/1943 | Balcar | 549/542 |
| 2,636,906 | 4/1953 | Davis | 260/633 |
| 2,756,241 | 7/1956 | Courter | 568/867 |
| 3,851,043 | 11/1974 | Gunther | 423/245 |
| 3,904,656 | 9/1975 | Broz | 568/867 |
| 3,988,421 | 10/1976 | Rinaldi | 423/210 |
| 4,087,474 | 5/1978 | Convers et al. | 568/867 |
| 4,102,981 | 7/1978 | Woychesin et al. | 570/177 |
| 4,112,054 | 9/1978 | Feingold et al. | 423/245 |
| 4,149,901 | 4/1979 | Morales | 127/12 |
| 4,165,440 | 8/1979 | Kim | 268/867 |
| 4,349,417 | 9/1982 | Rebsdat et al. | 568/867 |

FOREIGN PATENT DOCUMENTS

| | | | |
|---|---|---|---|
| 101201 | 5/1937 | Australia | 549/542 |
| 12405 | 5/1975 | Japan | 570/177 |

OTHER PUBLICATIONS

Morrison et al., *Organic Chemistry*, Second Edition, pp. 887ff, 1966.

*Primary Examiner*—J. E. Evans
*Attorney, Agent, or Firm*—Fleit, Jacobson, Cohn & Price

[57] ABSTRACT

A high efficiency process for removal and detoxification of olefin oxides from gas compositions is described. The process consists of olefin oxide absorption at ambient pressure in an absorber using an aqueous liquid as the absorbing medium and subsequent hydrolysis of the olefin oxide to products including an alkylene glycol in a chemical reactor operating at a controlled temperature and pH in the presence of an acid catalyst. The absorption stage is favored by low temperature and high liquid to gas ratios. More than 99% of an olefin oxide contained in a gas stream can be effectively removed in the absorption stage. The hydrolysis stage is favored by low pH conditions. More than 99% of the incoming olefin oxide to the reactor can be converted to alkylene glycols. The process has a capability of removing and detoxifying olefin oxide from gas streams with an overall effectiveness exceeding 98%. The process also provides for recovering inert diluent contained in the gas compositions.

13 Claims, 2 Drawing Sheets

PROCESS FOR OLEFIN OXIDE DETOXIFICATION

This application is a continuation-in-part of Ser. No. 521,955, filed Aug. 10, 1983, now abandoned, which is in turn a continuation-in-part of Ser. No. 409,830, filed Aug. 20, 1982, now abandoned.

BACKGROUND OF THE INVENTION

This invention relates to a process for removing olefin oxides, such as ethylene oxide and propylene oxide, from gas compositions containing such, and more particularly to a process for removing ethylene oxide in exhaust gases discharged from ethylene oxide sterilizers.

Ethylene oxide sterilizers are typically utilized, for example, in hospitals and medical product manufacturing facilities for treating articles such as plastic, paper, rubber or the like which cannot withstand heat sterilization. Sterilization is effected when ethylene oxide reacts with contaminating microorganisms to kill or inactivate them.

The sterilization process is typically carried out in a chamber which is evacuated after the articles to be treated are placed within. Either one-hundred percent ethylene oxide or an admixture with an inert diluent such as dichlorodifluoromethane or carbon dioxide is then introduced to the chamber and allowed to remain therein until the sterilization process is completed, usually from about 1 to 8 hours. After the sterilization period is completed, the gas in the chamber is exhausted and the sterilized articles removed. In order to ensure safe worker exposure levels, it may be necessary to exhaust the chamber in a series of post-evacuations prior to entry into the chamber. Ethylene oxide may be discharged to the environment with each post-evacuation, although concentrations will decrease with each successive evacuation.

A number of evacuations are needed because the product may absorb relatively substantial amount of the olefin oxide, which off-gasses from the product only gradually. At the end of post-evacuations, the chamber may be ventilated with relatively high flow rates of air. This air containing small amounts of off-gassed olefin oxide is ordinarily released into the environment. Even after the sterilized product is removed from the chamber, additional amounts of olefin oxide may be released into the work place because of off-gassing from the product. Because olefin oxide is off-gassed or diffuses out of the product with time, this is the major reason that sterilization plants quarantine the products, preferably in an isolated area after exposure to olefin oxide. The quarantined areas are ordinarily heavily ventilated to reduce worker exposure to the fumes. The small amounts of olefin oxide which are caught-up in the ventilation system are ordinarily released into the environment.

Due to the highly toxic nature of ethylene oxide, special precautions must be taken to assure proper ventilation to the area. Generally, ventilation systems are provided to direct ethylene oxide outside of the building. However, such systems are not entirely satisfactory from an environmental protection standpoint, particularly because there is still the possibility that human receptors outside of the building may unknowingly come into contact with the ethylene oxide before it has been sufficiently dispersed in the ambient atmosphere. Moreover, unfavorable meteorological conditions can contribute to unacceptably high ground level ambient ethylene oxide concentrations and/or hazardous in-plant worker exposure levels due to ethylene oxide recirculation back into the building. Such concern becomes paramount with the acceptable ethylene oxide worker exposure level reduced below one part per million. Consequently, a means must be provided to control the venting of ethylene oxide, particularly in any areas where human receptors can be exposed to such releases.

In view of increased concern over the environment, various methods have been devised by the art in an attempt to remove toxic olefin oxides, such as ethylene oxide and propylene oxide, from exhaust gases containing such. For example, U.S. Pat. No. 3,851,043 to Gunther discloses a method of treating exhaust gases from ethylene oxide sterilizers by passing the exhaust gas through a column containing a strong acid, cationic active ion exchange resin in the hydrogen form. The Gunther patent also discloses the use of an oxidizing resin manganese green sand in place of the ion exchange resin. The process taught by Gunther is a single step, batch process, having the disadvantage that the absorption beds must be either regenerated or disposed of once they have become saturated.

It is well-known in the art that olefin oxides can be hydrolyzed to alkylene glycols, which in dilute solutions are not considered to be environmentally hazardous. These acid catalyzed reactions are described by Morrison and Boyd, *Organic Chemistry*, Second Edition, pp. 887ff, 1966, and U.S. Pat. Nos. 1,641,710, 2,636,906 and 4,165,440.

U.S. Pat. No. 4,112,054 to Feingold et al discloses a method of removing ethylene oxide from gaseous mixtures by passing the gas through an aqueous acidic solution to simultaneously dissolve the ethylene oxide and convert the ethylene oxide to ethylene glycol and other products at a pH of less than 4 and an initial temperature of 50 degrees C. The Feingold et al patent is directed toward relatively small hospital sterilizers, and particularly toward a sterilizing means which can be rendered portable, to afford quick and efficient use. In addition, the Feingold et al process is disclosed as having an efficiency of 97% using acids such as oxalic acid, sodium bisulfate, hydrochloric acid, and hydrobromic acid. Of the acids described by Feingold et al as being most efficient, halogenated acids will produce halohydrin by-products, i.e., ethylene bromo-and chlorohydrins, which are considered highly toxic substances, and oxalic acid is extremely expensive and not cost effective. In addition, in their process, Feingold et al absorb and convert the olefin in one step. Therefore, the absorption of ethylene oxide cannot be optimized, and the conversion to alkylene glycols likewise cannot be optimized since the exothermic heat of solution using an acidic solution to absorb the olefin oxide reduces the dissolution rate. The Feingold et al patent is also a batch process and limited in application to sterilizers which do not use steam ejectors for evacuation.

U.S. Pat. No. 2,135,271 to Balcar is directed toward a method of optimizing glycol production. Disclosed is a cyclic method wherein an olefin oxide is absorbed and converted via thermal hydrolysis to an alkylene glycol, an the alkylene glycol solution is then recycled back to the absorber to absorb more olefin oxide until the concentration of the alkylene glycol reaches a point where it is commercially economical to separate the glycol from solution. The Balcar patent is not concerned with the efficiency of removing olefin oxides from gaseous mixtures.

Accordingly, it is an object of this invention to provide a highly efficient process for removing olefin oxides from gas mixtures containing olefin oxides in order that environmental hazards may be greatly reduced.

A further object of the present invention is to provide for the removal of olefin oxides from gas compositions in a process useable on an industrial scale.

A further object of tis invention is to remove at ambient pressure more than about 99% of olefin oxides from a gas composition containing such.

A further object of the invention is to provide a process for converting more than about 99% of the olefin oxides into substances which are not environmentally dangerous.

A further object of the invention is to provide a process wherein olefin oxides can be efficiently converted to alkylene glycols using sulfuric acid as a catalyst, which does not convert to toxic substances, and is relatively inexpensive to use.

A further object of the invention is to provide a process wherein olefin oxides that are "off-gassed" from the product either during chamber ventilation or in quarantine areas and released into a ventilation system can be removed from the ventilation streams.

A further object of the invention is to provide a process wherein the inert diluent for the olefin oxides is recovered.

A further object of the invention is to provide a process wherein the alkylene glycol generated by the reaction of olefin oxide with water is biodegraded into carbon dioxide and water.

Further objects of the invention will become apparent from the following description and claims.

BRIEF DESCRIPTION OF THE DRAWING

The FIGURE illustrates a flow diagram for the claimed olefin oxide detoxification process.

SUMMARY OF THE INVENTION

This invention provides a method for removing olefin oxides from gas compositions, and converting such into alkylene glycols. The process for removing olefin oxides is essentially a two-stage process wherein the olefin oxide is absorbed in a neutral or acidic absorbing liquid and is thereafter transferred to a reactor, together with an acid catalyst, wherein the absorbed olefin oxide is converted to alkylene glycols. Thereafter, the reaction products, consisting essentially of water, acid catalyst, and alkylene glycol, from the reactor can be recycled back to the absorber after appropriate cooling or neutralized using an alkali, and the neutralized, non-toxic reaction product stream can be either transferred to a water treatment system, or safely discharged to a drain. Accordingly, the present invention provides a process for removing an olefin oxide from a gas composition containing such by contacting the gas composition with an aqueous liquid to absorb the olefin oxide in solution, and converting the olefin oxide by hydrolysis to products including alkylene glycol using an acid catalyst.

The present invention further provides a process for removing an olefin oxide from a gas composition by contacting the gas composition with an aqueous liquid, causing absorption of the olefin oxide into the aqueous liquid, and feeding the aqueous solution containing the absorbed olefin oxide and an acid catalyst into a reactor, and reacting the aqueous solution for a time sufficient to substantially convert the olefin oxide to products including alkylene glycol, and recycling the glycol solution after cooling back to the absorption column. Once-through operation may necessitate neutralizing the aqueous reaction product stream with an alkali.

Further, the present invention provides a continuous process for removing an olefin oxide from a gas composition by contacting said gas composition with an aqueous liquid, causing absorption of the olefin oxide into the aqueous solution, and feeding the aqueous solution containing the absorbed olefin oxide and an acid catalyst into a reactor, and reacting the aqueous solution for a time sufficient to substantially convert the olefin oxide into products including an alkylene glycol while continuously removing sufficient quantities of the aqueous reaction product stream from the reactor to keep the volume of solution in the reactor constant and recycling this stream back to the absorber.

Further, the present invention provides a means for removing an olefin oxide from plant ventilation streams including sterilization chamber ventilation following post-evacuations. The "off-gassed" olefin oxide from the ventilation stream is captured on an adsorbent carbon bed. Periodically, when the apparatus for evacuating the sterilizer is not ordinarily in use, the carbon in the carbon bed may be regenerated by removing the olefin oxide therefrom by vacuum and subjecting the removed olefin oxide to the process described above for the treatment of the olefin oxide that is removed from the sterilizer.

Further, the present invention provides a process for recovering any inert diluent such as dichlorodifluoromethane from the olefin oxide-free gas stream exiting the absorber. The olefin oxide-free gas stream is fed into a wash tower and a dessicant dryer to reduce the moisture and acid content. The gas is compressed to a high pressure before entering a series of filters to remove particulates and other foreign matter. Partial gas condensation is then effected in a heat exchanger. The gas and liquid streams exiting the heat exchanger are fed into a separator, where the gas stream is vented directly to the atmosphere and the liquid is directed to a different series of filters for final purification of the recovered inert diluent.

DESCRIPTION OF THE PREFERRED EMBODIMENTS

Figure 1:
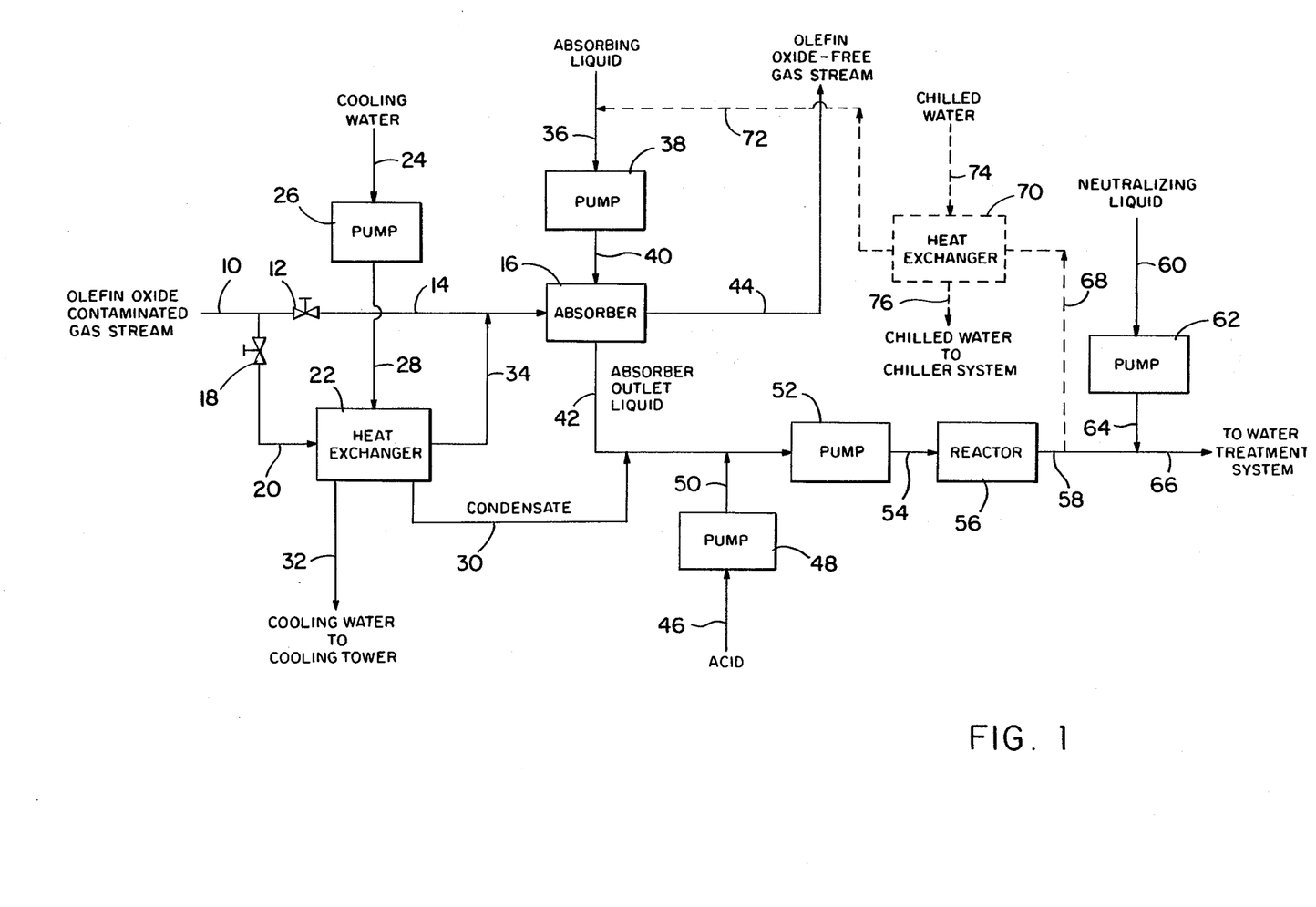

The process flow diagram of the olefin oxide detoxification system is shown in FIG. 1. The olefin oxide contaminated gas stream enters the system through line 10. The olefin oxide, such as ethylene oxide, concentration can range anywhere from 0 to 100% by volume. In view of the explosive nature of ethylene oxide in air, rarely will a 100% ethylene oxide discharge stream to the atmosphere be encountered in industrial practice. More typically, the gas stream will consist of an ethylene oxide admixture with an inert diluent such as dichlorodifluoromethane, carbon dioxide or steam. Gas streams with a diluent, such as dichlorodifluoromethane or carbon dioxide, are directed through valve 12 into line 14 to absorber 16. Gas streams with a condensable diluent, such as steam discharged from an ejector evacuating an ethylene oxide sterilizer, are directed through valve 18 into line 20 to heat exchanger 22. When valve 12 is open, valve 18 is closed. When valve 18 is open, valve 12 is closed. Cooling water supplied via line 24 is pumped to heat exchanger 22 by pump 26 via line 28 to condense the condensable portion of the ethylene oxide contaminated gas stream. Liquid condensate containing a portion of the ethylene oxide is then fed via line 30 and mixed with the absorber 16 outlet fluid stream. Cooling water from heat exchanger 22 is fed to a cooling tower or the like via line 32. Vapors from heat exchanger 22 are directed through line 34 to absorber 16. The gas stream is contacted with an aqueous liquid in absorber 16 wherein the olefin oxide present in the gas stream is absorbed by the aqueous liquid and removed from the gas stream.

Absorber 16 is an absorption vessel, typically either filled with a bed of packing materials or containing any of the various types of trays (e.g., sieve trays, bubble-cap trays, etc.) arranged one above the other, which provides a large surface area for contact between the aqueous absorbing liquid and the olefin oxide-contaminated gas. The transfer of olefin oxide from the gas phase to the liquid phase takes place primarily on the packing surface or on the trays. Any type of absorber which provides sufficient contact surface area may be used for olefin oxide absorption. The absorbing liquid which may be the reactor product stream after appropriate cooling is supplied to the detoxification system via line 36 and is pumped to the absorber by pump 38 via line 40. The absorbing liquid absorbs olefin oxide from the gas stream in the absorber and leaves the absorber via line 42. Other ethylene oxide contaminated liquid streams such as the condensate from heat exchanger 22 or the discharge water from any liquid ring vacuum pumps on the sterilizers may be added to the absorber outlet liquid stream in line 42. The substantially olefin oxide-free gas leaves the absorber via line 44 and may be discharged into the atmosphere or, in the case of gas streams with a diluent, such as dichlorodifluoromethane, may be recovered in the recovery system shown in FIG. 2. Under appropriate operating conditions, at least about 99% of the olefin oxide in the gas composition is absorbed.

An acid is added to the olefin oxide liquid solution upstream of reactor 56 to achieve the desired pH. The acid is supplied to the detoxification system via line 46 and is added to the liquid by metering pump 48 via line 50. The now acidulated liquid is pumped to reactor 56 by pump 52 via line 54. Olefin oxide reacts with water to form alkylene glycol in the reactor 56. The extent of olefin oxide conversion to alkylene glycol depends primarily upon the liquid pH, reaction temperature and residence time. Sufficient residence time and adequate mixing are provided in reactor 56 to convert, under appropriate operating conditions, at least about 99% of the olefin oxide to alkylene glycol under the prevailing conditions of temperature and pH. The reaction products leave the reactor via line 58 and essentially consist of water, acid catalyst and alkylene glycol. The acid in the aqueous solution leaving the reactor can be neutralized with an alkali. The neutralizing agent is supplied to the detoxification system via line 60 and is added to the liquid stream by pump 62 via line 64. The neutralized liquid stream leaves the detoxification system via line 66 and may be discharged directly to a sanitary drain or directed to a water treatment facility. Alternatively, in a recycle operation, the aqueous solution of ethylene glycol leaving the reactor is sent to heat exchanger 70 via line 68, where it is cooled using chilled water. The cold stream of ethylene glycol solution leaving heat exchanger 70 is recycled back to the absorbing liquid supply line 36 via line 72, and pumped back to the absorber by pump 38 via line 40 for further absorption of olefin oxide. The chilled water is supplied to heat exchanger 70 via line 74 and is sent back to a chiller system for reuse via line 76. In the recycle process, acid need be introduced only at the beginning of the operation since the acid catalyst is not consumed in the reaction.

The process of the present invention is designed to remove olefin oxides, having either 2 or 3 carbon atoms, i.e., ethylene oxide or propylene oxide, from a gas stream, and to chemically convert the oxides by hydrolysis to less environmentally hazardous products.

The absorption of the olefin oxide is carried out in any conventional type of absorber, for example, packed towers, plate columns, etc., which provide a high degree of gas-liquid contact. Any conventional type of packing material may be used. Preferably, the absorption is carried out in a packed counter-current scrubber. Preferably, the scrubber will contain a packing material which provides a large contact surface area per unit packed volume. For example, plastic packing material having a diameter of about $\frac{1}{2}''$ to $2''$ may be used.

For the purposes of the invention, any aqueous liquid that satisfactorily absorbs olefin oxides may be used. For example, waste water that is recycled from other processes may be used. In general, the preferred pH range of the absorbing liquid is between 0.2 and 8, more preferably between about 0.5 and 7.5. For non-recycle operation, the preferred pH range of the absorbing liquid is between 4 and 8, more preferably between about 6.5 and 7.5. In a recycle process, however, the preferred pH range of the absorbing liquid is between 0.2 and 4, more preferably between about 0.5 and 2. The amount of ethylene glycol in the absorbing liquid ranges preferably from 0 to 70% by weight, more preferably from 0 to 40% by weight. The absorbing liquids having pH values outside the preferred ranges may also be used as pH values will have a minimum impact on the absorption process and will primarily affect acid catalyst requirements. If the pH of the absorbing liquid is low, the relatively small residence time of the liquid in the absorption column as compared to that in the reactor is insufficient to achieve any significant degree of conversion in the absorber. However, less acid catalyst will be required. On the other hand, if the pH of the absorbing liquid is high, acid catalyst requirements upstream of the reactor will be increased in order to achieve the desired degree of conversion to glycol in the reactor.

The absorption of olefin oxide is favored by high liquid-to-gas ratios. The process is normally conducted at liquid-to-gas ratios, i.e., absorbing liquid flow rate/gas stream flow rate ratio of about 40 to 500 gallons/1000 ft$^3$. Preferably, the liquid-to-gas ratios will be maintained at about 100 to 300 gallons/1000 ft$^3$, more preferably about 60 to 70 gallons/100 ft$^3$. The absorbing liquid may be supplied to the absorber through spray nozzles installed above the main packed volume or trays. Gas containing the olefin oxide is introduced at the bottom. The liquid and the gas streams are made to contact counter-currently in the absorber where more than about 97% to 98%, and preferably more than about 99% of the olefin oxide is absorbed from the gas stream into the absorbing liquid with the absorption column operating essentially at ambient pressure. The clean gas exits the absorber at the top. The liquid leaving the bottom of the absorber is an aqueous solution of olefin oxide and/or alkylene glycol.

The amount of olefin oxide in the gas stream can be between 0 and 100% by volume. More typically, the olefin oxide in the gas stream will range from about 50 ppm to 90%, even more typically about 1000 pm to 50%, by volume. Most typically, the amount of olefin oxide in the gas stream will be from about 1 to 30% by volume.

Generally, the gas temperature at the inlet of the absorber will be less than about 500 degrees F. It is preferred that the temperature at the gas inlet be less than about 230 degrees F., and generally the temperature will be less than about 140 to 150 degrees F. In general, the gas may flow into the absorber at any rate that may be convenient. In the case of an extremely high gas flow rate, the process can merely be adjusted by increasing the flow rate of the absorbing liquid so long as the absorber has been designed to treat the extremely high gas flow rate.

For the purposes of this invention, the liquid solution upon leaving the absorber will typically contain less than about 5% by weight of olefin oxide, and 0 to 70% by weight of alkylene glycol. In general, the absorbing liquid entering the absorber contains less than about 100 ppm by weight of an olefin oxide and less than about 70% by weight of alkylene glycol.

The absorbing liquid entering the absorber can be maintained at less than about 80 degrees F. Preferably, the temperature will be less than about 70 degrees F. and, most preferably, the temperature will be less than about 60 degrees F. If tap water or fresh water is used, the temperature of the absorbing liquid will vary as the temperature of the water in the pipes. As will be appreciated by those skilled in the art, the absorbing liquid will lower the temperature of the gas in the gas stream, and in the case where the gas stream temperature is extremely high, lower absorbing liquid temperatures will be preferred since absorption is facilitated at lower temperatures.

For convenience, in the preferred embodiment of the present invention, the acid catalyst is added to the liquid stream after it leaves the absorber and before it reaches the reactor. Any acid producing hydrogen ions in solution can be used. The preferred mineral acid is sulfuric acid. As is known to those skilled in the art, dilution of concentrated acids, and particularly dilution of sulfuric acid, is strongly exothermic. Accordingly, the temperature of the absorbing liquid entering the reactor may be considerably higher than the temperature of the absorbing liquid leaving the absorber.

After addition of the catalyst, the absorbing liquid solution is processed in a reactor operating in a continuous mode. Any type of reactor can be used in the present process that provides the proper degree of mixing and residence time for the chemical reaction to occur. For example, a constant flow stirred tank reactor, a batch-type reactor, or a plug flow type reactor can be used. The olefin oxide solution is fed into the reactor at a constant rate and the processed liquid is discharged at the same rate. In general, any liquid flow rate can be handled by the reactor as long as the proper degree of mixing and residence time, for the size of the reactor, is maintained.

Hydrolysis of the olefin oxide to the corresponding alkylene glycol is favored by low pH conditions. As discussed above, in the preferred embodiment of the invention, in general, the absorbing liquid entering the reactor will contain less than about 5% by weight of olefin oxide, and less than about 70% by weight of alkylene glycol. The proper degree of mixing is provided in the reactor. The retention time needed for substantially complete hydrolysis of the olefin oxide is dependent on the hydrogen ion concentration in the reactor, the temperature and the liquid flow pattern in the reactor. In general, for a tubular flow reactor treating an ethylene oxide contaminated liquid stream at a pH between about 0.5 and 2.0 and a temperature between about 70 degrees F. and 100 degrees F., preferably between about 60 to 80 degrees F., the retention time of the liquid in the reactor can range between about 1 minute and 3 hours. The retention time will range preferably between about 1 minute and 1 hour, and most preferably between about 30 minutes and 60 minutes.

In general, the temperature of the liquid entering the reactor will be less than about 120 degrees F., preferably about 100 degrees F. In general, chemical reaction will take place in the reactor at atmospheric pressure or slightly above. Under the operating conditions of the process, more than about 99% of the olefin oxide present in the liquid stream can react with water to form alkylene glycol.

The conversion of the olefin oxide to alkylene glycol can be facilitated using any acid which ionizes to provide hydrogen ions in solution, for example, sulfuric acid, phosphoric acid, etc. As discussed above, for reasons of economics, and safety, the most preferred catalyst is sulfuric acid. In general, the concentration of hydrogen ion catalyst used in the process will be about 0.1 molar, although the preferred range is from about 0.01 to 1 molar. The most preferred range of hydrogen ion concentration is from 0.03 to 0.3 molar since the cost of the catalyst is reduced.

In general, the mole ratio of acid to olefin oxide will be between about 0.001 and 250, preferably between about 0.005 and 200, and most preferably between about 0.01 and 25, and the pH of the reactants entering the reactor will be preferably about 0 to 2.

The liquid stream leaving the reactor in the process of the invention is an aqueous solution of alkylene glycol which contains a negligible amount of unreacted olefin oxide. The concentration of alkylene glycol in the liquid leaving the reactor typically will be less than about 70% by weight. Generally, for the purposes of the preferred embodiment, it will be less than about 70% by weight. This liquid stream is either recycled after appropriate cooling back to the absorber or neutralized with an alkali and safely disposed of.

For purposes of this invention, for once-through operation, after the liquid stream leaving the reactor has been neutralized, it will be released into the environment Any alkaline chemical which can produce hydroxyl ions in solution can be used to neutralize the hydrogen ions of the catalyst. For example, alkali metal and alkaline earth metal hydroxides, such as potassium hydroxide, magnesium hydroxide, calcium hydroxide, or sodium hydroxide, etc. can be used. Most preferably, sodium hydroxide will be used. In recycle operation, the concentration of alkylene glycol in the aqueous solution leaving the reactor will increase this time as more and more olefin oxide is absorbed in the absorber and hydrolyzed to alkylene glycol in the reactor. When the alkylene glycol concentration in the reactor outlet stream reaches at least about 70% by weight, the relatively concentrated, aqueous solution of alkylene glycol will be removed from the entire system and disposed of safely. The system will subsequently be filled with fresh water for olefin oxide absorption and hydrolysis.

The alkylene oxide hydrolysis reaction takes a finite amount of time and, even under optimum conditions, there will always be, at any given time, unconverted olefin oxide in solution. This unconverted olefin oxide in solution is very sensitive to temperature, and a relatively small rise in temperature can cause a decrease in the olefin oxide solubility in the absorbing liquid composition. Since dilution of the preferred sulfuric acid catalyst is a strongly exothermic reaction, and hydrolysis of the olefin oxide is also an exothermic reaction, the temperature of the liquid in the reactor, in general, will be higher than the temperature of the liquid leaving the absorber. Since the reactor is closed, partial pressures of the gases dissolved in the liquid from the scrubber may raise the pressure in the reactor to slightly above atmospheric. Since the reactor is closed, however, as olefin oxide is hydrolyzed to the corresponding alkylene glycol, gas will be absorbed, and consequently also hydrolyzed, thereby making possible complete hydrolysis of nearly all of the olefin oxide absorbed from the gas stream. Complete hydrolysis takes place, despite the fact that there is a slight lag or induction period before hydrolysis of an olefin oxide begins when using sulfuric acid as a catalyst. This lag or induction period is presumed to be one of the reasons that prior art processes were not capable of removing more than 94% of the olefin oxide when using a single step absorption-reaction process with a sulfuric acid catalyst.

On an industrial scale, more than one absorber may be used. In such a case, olefin oxides which have been absorbed by the absorbing liquid in more than one absorber may be fed into a single reactor. In addition, other olefin oxide liquid solutions from other contamination sources may also be fed into the reactor and similarly may be converted to the corresponding alkylene glycol.

Also, some gas streams may also contain steam (for example, the exhaust gas from a sterilizer equipped with steam ejectors for evacuation), and the gas temperature can be as high as about 300 degrees F. or more. If the olefin oxide-contaminated gas mixture contains steam, the gas may be passed through a heat exchanger as illustrated in the figure. The heat exchanger can be used to condense virtually all of the steam present in the contaminated gas. Cooling water can be used for this purpose. The heat exchanger provides an indirect contact between the cooling water and the gas stream to reduce the gas temperature below saturation temperature. This condenses most of the steam and a small portion of olefin oxide present in the gas stream, and simultaneously causes a rise in the cooling water temperature. The relatively hot cooling water leaves the heat exchanger and is sent to a cooling tower for reuse. The relatively cool gas leaves the heat exchanger and enters the absorber. The condensate primarily would consist of a very dilute solution of olefin oxide in water. This condensate stream can be mixed with the liquid stream from the absorber for further treatment in the reactor. The heat exchanger may also be used to cool the olefin oxide-contaminated gas stream, if necessary, even if the gas stream does not contain steam. The heat exchanger may be excluded from the detoxification system if there are no cooling requirements.

As described above, the product, after being subjected to sterilization, is aerated in the chamber for a certain period of time and/or isolated in an isolation area since it retains a certain amount of olefin oxide thereon, which cannot be removed during the evacuation of the sterilizer. The off-gassed olefin oxide is diluted in the ventilation air and removed by ventilating the chamber and/or isolation area. In order to prevent as much olefin oxide as possible from escaping int the environment, it is preferred that additional steps be taken to remove olefin oxide from the ventilation streams of the isolation area and the chamber.

Since the above-described apparatus is very cost sensitive to the flow rate of gas which is to be treated, it is not economically practical to design the apparatus large enough to handle the high gas flow rate ventilation streams encountered while the product is off-gassing. Therefore, the apparatus is sized to operate only during the evacuation(s) of the sterilizer.

Since the ventilation as flow rates are relatively large compared to the vacuum pump flow rates during evacuation of the sterilization chamber, and the ventilation streams contain relatively low concentrations of olefin oxide, and since the ventilation systems (except chamber ventilation) operate continuously, we have found that it is most practical to adsorb and concentrate the "off-gassed" olefin oxide as it is removed from the ventilation stream onto an adsorbent, for example, a carbon adsorbent, and to regenerate the adsorbent on, for example, a daily basis, and subject the olefin oxide removed from the adsorbent to the above-described process.

According to the present invention, a carbon adsorbent preferably will be used, although it should be recognized that any adsorbent suitable for adsorbing an olefin oxide can be used. Using such a method, the apparatus described above may be used to neutralize the olefin oxide at a time when the apparatus would not ordinarily be operating.

In accordance with this embodiment, air, from the ventilation system, containing olefin oxide, which is removed from the "off-gassing" product, is passed through air ducts over a carbon bed. Preferably, activated carbon, such as activated charcoal, is used. Since the olefin oxide concentrations in the ventilation system are extremely low, it ordinarily will take a considerable amount of time to saturate a carbon bed. Therefore, the system could be designed for regeneration once every 24 hours. Longer or shorter times may be used depending on the needs. In this manner, regeneration can take place at a time when the vacuum pump and the apparatus are not ordinarily in use. The carbon beds used in the ventilation system can be regenerated individually, and it is therefore possible to develop a sequence for regenerating individual carbon beds while the carbon beds associated with separate vent systems continue to adsorb olefin oxide from the ventilation streams. Regeneration of each carbon bed can be cycled appropriately and controlled automatically by the apparatus.

It is noted that the size of the carbon bed will control the frequency of the regeneration needed. The size of the carbon bed and frequency of regeneration can be determined by site-specific plant requirements and operating conditions. In the preferred embodiment of the invention, just prior to regeneration of the carbon bed, the individual carbon bed can be isolated by an appropriate valving system. During regeneration, the vacuum damper would open and the existing sterilizer vacuum pump, described above, would pull off the adsorbed olefin oxide. This concentrated olefin oxide stream would then be discharged into the apparatus as described above. As is recognized by those skilled in the art, the carbon bed system is designed to structurally withstand the required vacuum conditions. Also, appropriate precautions are taken to prevent explosion hazards. By the above-described means, more effective use of the existing apparatus can be made, and more total ethylene oxide can be detoxified.

Figure 2:
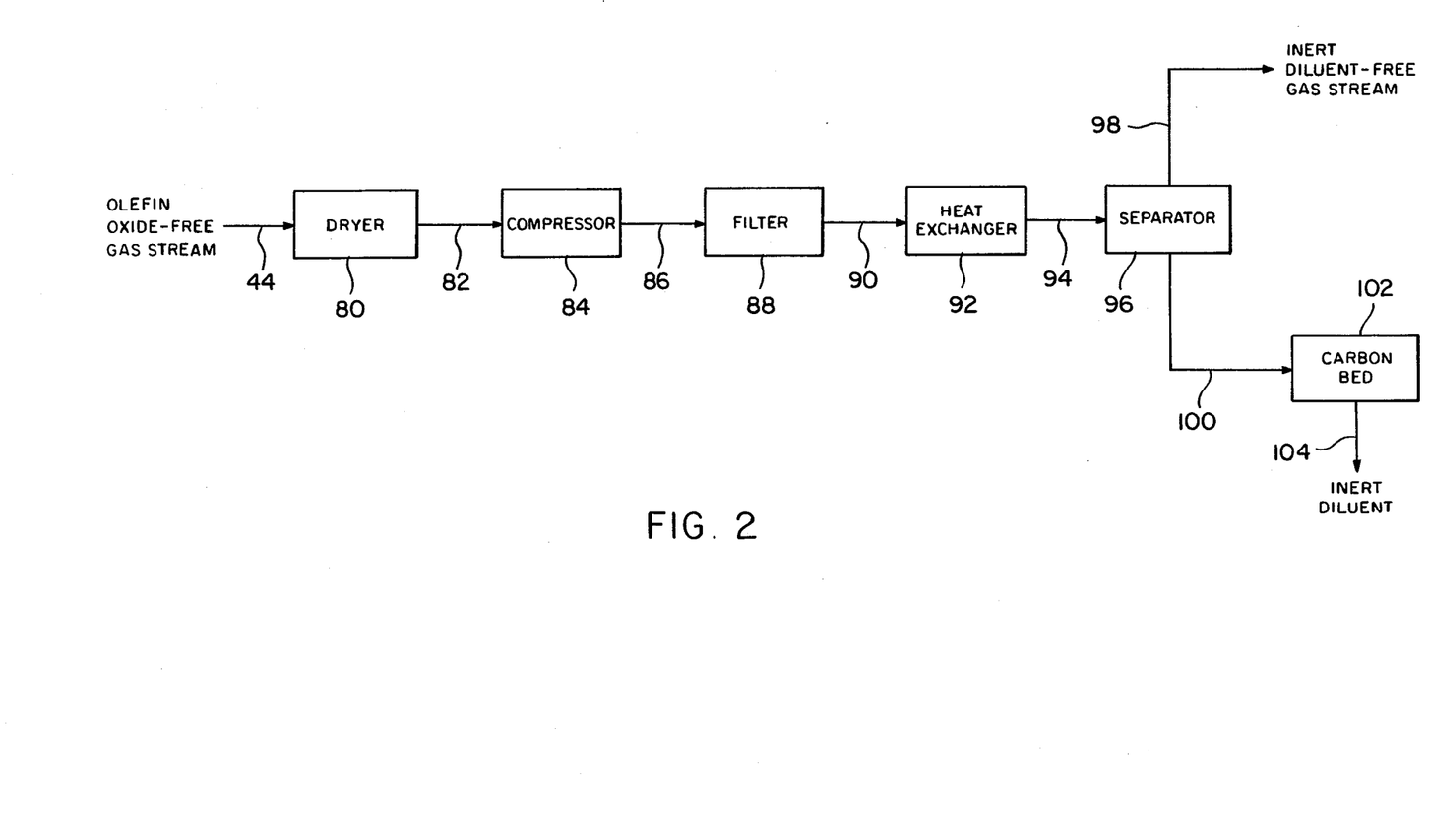

If the olefin oxide-free gas stream leaving the absorber via line 44 contains an inert diluent, such as dichlorodifluoromethane, the inert diluent is recovered as shown in FIG. 2. The olefin oxide-free gas stream will typically contain about 0 to 90% by weight of an inert diluent. The olefin oxide-free gas stream will have a temperature of about 60 to 80 degrees F. In order to recover the inert diluent, the olefin oxide-free stream is directed to dryer 80. Dryer 80 is a fixed-bed dessicant dryer designed to remove the moisture from the gas stream. The gas stream is then fed via line 82 to compressor 84. Compressor 84 compresses the gas to a high pressure, preferably 130 to 170 psig. The gas stream is then fed via line 86 to a series of filters (88). The filters will remove the particulates and other foreign matter. The gas stream is then fed via line 90 to heat exchanger 92. Partial gas condensation is then effected in heat exchanger 92. The gas/liquid temperature after cooling is preferably about −20 to 50 degrees F. The heat exchanger 92 is typically a shell-and tube heat exchanger. The gas and liquid streams exiting heat exchanger 92 are fed via line 94 to separator 96. The gas stream is vented directly to the atmosphere via line 98 and the liquid is directed via line 100 to a carbon bed 102, preferably an activated carbon bed, for final purification of the inert diluent. The recovered inert diluent exiting the recovery system via line 104 has a purity of greater than about 99% by weight. It will be understood that if the olefin oxide-free gas stream leaving the adsorbent bed discussed, supra, contains an inert diluent, the inert diluent from this stream also may be recovered as shown in FIG. 2.

DESCRIPTION OF THE BIODEGRADATION PROCESS

The continuous recycle mode employed in the invention results in an increase in the amount of ethylene glycol in the system as more and more ethylene oxide is absorbed and reacted. Thus, in accordance with another aspect of the invention, when the system attains 30-70% (by weight) ethylene glycol, the process liquid is neutralized and removed from the system to a separate holding tank for processing. This by-product solution, which contains ethylene glycol, sodium sulfate, water, and small amounts of polyethylene glycol, is fed at a controlled rate to a bioreactor where the glycols are degraded by bacterial action. The residence time employed in the reactor will vary from system to system, but, in general, it will be a minimum of 30 days.

The operation of the bioreactor requires controlling the liquid flow rate into and out of the reactor below a specified value (usually under 10 gallons per hour). In addition, an air handling system is used to transfer oxygen into the bioreactor. Dissolved oxygen will be maintained at levels above 0.1 mg/l. Since the degradation of glycols produces carbon dioxide which results in the increase in the acidity of the reaction liquid, a caustic such as sodium hydroxide is used to maintain the pH of the reaction mixture at 6.5-8.5.

Approximately 90% of the glycols entering the bioreactor will be removed. The by-product solution of the bioreactor will contain a small amount of glycols, and hence, can be discharged to the appropriate destination without further processing.

The following examples are provided to illustrate the preferred embodiments of the invention and are not intended as limitations on the process.

EXAMPLE 1

187 actual cubic feet per minute of a gas mixture at 60 degrees F. consisting of 24.2% by weight ethylene oxide and 75.8% by weight nitrogen was discharged to a 12 inch diameter column packed to a height of 6.0 feet with 1 inch TELLERETTE packing manufactured by the Ceilcote Company in Berea, Ohio. 12.3 gallons per minute of fresh water at 60 degrees F. was used as the scrubbing medium to absorb ethylene oxide using counter-current contact. 99.25% of the ethylene oxide was removed from the gas stream entering the absorber. The absorbing liquor exiting the bottom of the packed tower at 60 degrees F. containing 3.6% by weight ethylene oxide was pumped to a holding tank from which the ethylene oxide contaminated solution was pumped at a controlled flow rate of 2 gallons per minute to a 175 gallon continuous stirred tank reactor containing internal baffles and a ½ horsepower agitator. 5.0 molar sulfuric acid solution was fed to the reactor at a flow rate of 150 milliliters per minute to maintain a pH of 1.01 in the reactor. The reactor temperature was 83 degrees F. and liquid residence time 87.5 minutes. 98.0% of the ethylene oxide in solution was converted to ethylene glycol. All ethylene oxide and ethylene glycol determinations were made by gas chromatography with simultaneous measurements at the inlet and outlet of the absorber and reactor.

EXAMPLE 2

202 actual cubic feet per minute of a gas mixture at 60 degrees F. consisting of 31.8% by weight ethylene oxide and 68.2% by weight nitrogen gas was discharged to a 12 inch diameter column packed to a height of 6.0 feet with 1 inch TELLERETTE packing. 12.4 gallons per minute of fresh water at 60 degrees F. was used as the scrubbing medium to absorb ethylene oxide using counter-current contact. 99.3% of the ethylene oxide was removed from the gas stream entering the absorber. All ethylene oxide determinations were made by gas chromatography with simultaneous measurements at the inlet and outlet of the absorber.

EXAMPLE 3

To evaluate the importance of pH on the ethylene oxide-ethylene glycol reaction, the pH in the reactor was increased to 2.10. An aqueous liquor at 60 degrees F. containing 3.4% by weight ethylene oxide was pumped at a controlled flow rate of 2 gallons per minute to a 175 gallon continuous stirred tank reactor containing internal baffles and a ½ horsepower agitator. 5.0 molar sulfuric acid solution was fed to the reactor at a flow rate of 15 milliliters per minute to maintain the desired pH of 2.10 in the reactor. The reactor was operated at an average temperature of 115 degrees F. with a liquid residence time of 87.5 minutes. 93.8% of the ethylene oxide in solution was converted to ethylene glycol. All ethylene oxide and ethylene glycol determinations were made by gas chromatography with simultaneous measurements at the inlet and outlet of the reactor.

EXAMPLE 4

A gas mixture at 120 degrees F. consisting of 22.9% ethylene oxide, 61.3% dichlorodifluoromethane, 2.5% water, and 13.3% air (by volume) was charged at 50 actual cubic feet per minute to an 18" diameter absorption column. The column was packed to a height of 19' to 1" TELLERETTE packing manufactured by the Ceilcote company. A scrubbing liquid containing 40% ethylene glycol, 1% sulfuric acid, and 59% water (by weight) was fed into the absorption tower at a controlled rate of 10 gallons per minute. Under the above operating conditions, 99.2% (by weight) of the ethylene oxide entering the system was removed by absorption and reaction.

The gas stream exiting the absorption tower was fed into a dessicant dryer and a series of filters to remove the moisture and particulates. It was then compressed to a pressure of 150 psig and cooled down to 5 degrees F. Partial gas condensation was thus effected, resulting in the recovery of approximately 94% of the dichlorodifluoromethane entering the system. The recovered product was filtered and treated with activated carbon to yield a final product purity of 99.6% (by weight).

The 40% ethylene glycol solution was neutralized with sodium hydroxide and discharged to a 4,000 gallon storage tank. From the storage tank, the solution was fed into a 4,000 gallon bioreactor at a controlled rate of 3 gallons per hour. The liquid discharged from the bioreactor contained 4.3% (by weight) ethylene glycol.

As will be readily understood by those of ordinary skill in the art, minor modifications may be made in the invention described above without in any way departing from the spirit and scope of the invention. Accordingly, it is understood that the invention will not be limited to the exact details disclosed hereinabove, but will be defined in accordance with the appended claims.

What is claimed is:

1. In a continuous process for removing olefin oxide having 2 or 3 carbon atoms from exhaust gases containing an inert diluent discharged from ethylene oxide sterilizers, the improvement comprising removing at least about 97% of said olefin oxide from said exhaust gases containing said olefin oxide, converting at least about 97% of the olefin oxide into less environmentally hazardous substances and recovering the inert diluent having a purity of above about 99% by weight by:
   contacting said exhaust gases with an aqueous absorbing liquid at an absorbing liquid-to-gas flow rate ratio of about 40 to 500 gal/1000 ft$^3$ and absorbing at least about 97% of the olefin oxide into the aqueous liquid;
   feeding the aqueous liquid containing the absorbed olefin oxide and an acid catalyst into a reactor, said reactor being at atmospheric pressure or slightly above atmospheric pressure;
   reacting said aqueous liquid for a time sufficient to convert at least about 97% of the olefin oxide to products including an alkylene glycol while continuously removing sufficient quantities of aqueous liquid from the reactor to keep the volume of liquid in the reactor constant;
   compressing the olefin oxide-free exhaust gases after contact with the aqueous absorbing liquid to a pressure of about 130 to 170 psig;
   cooling the gas/liquid from the compressor to a gas/liquid temperature of about −20 to 50 degrees F.; and
   recovering the inert diluent having a purity above about 99% by weight.

2. The process of claim 1 wherein the initial pH of the absorbing liquid is between 0.2 and 8.

3. The process of claim 1 wherein the conversion of olefin oxide to alkylene glycol is catalyzed in the reactor by an acid producing a hydrogen ion concentration of about 0.01 to 1 gram-mole per liter.

4. The process of claim 1 wherein the hydrogen ion concentration of the acid catalyst in the reactor is about 0.03 to 0.3 gram-mole per liter.

5. The process of claim 1 wherein the reaction product liquid is cooled and recycled back to the absorber for further absorption of olefin oxide.

6. The process of claim 1 wherein the reaction product liquid is neutralized by an alkaline solution containing free hydroxyl anions as it is removed from the reactor.

7. The process of claim 1 wherein the acid catalyst is sulfuric acid.

8. The process of claim 1 wherein the volume of olefin oxide in the gas composition is between 0 and 90%.

9. The process of claim 1 wherein the olefin oxide is ethylene oxide.

10. The process of claim 1 wherein the initial temperature of the absorbing liquid is less than about 80 degrees F.

11. The process of claim 1 wherein the temperature of the aqueous liquid entering the reactor is less than about 120 degrees F.

12. In a continuous process for removing olefin oxide having 2 or 3 carbon atoms from exhaust gases containing an inert diluent discharged from ethylene oxide sterilizers, the improvement comprising
   contacting said exhaust gases with an aqueous absorbing liquid having a pH between about 0.5 and 7.5 and a temperature less than about 70 degrees F. causing absorption of at least about 97% of the olefin oxide into said aqueous liquid, said contacting being conducted at an absorbing liquid-to-gas flow rate ratio of about 40 to 500 gal/100 ft$^3$;
   feeding said aqueous liquid containing absorbed olefin oxide at a temperature of less than about 120 degrees F. into a reactor containing an acid catalyst at concentration of about 0.01 to 1 gram-mole per liter, said reactor being at atmospheric pressure or slightly above atmospheric pressure;
   reacting said aqueous liquid for a time sufficient to convert at least 97% of the olefin oxide to products including an alkylene glycol while continuously removing sufficient quantities of aqueous liquid from the reactor to keep the volume of solution in the reactor constant;
   compressing the olefin oxide-free exhaust gases after contact with the aqueous absorbing liquid to a pressure of about 130 to 170 psig;
   cooling the gas/liquid from the compressor to a gas/liquid temperature of about −20 to 50 degrees F.;
   separating an inert diluent-free gas stream from the inert diluent; and
   recovering the inert diluent having a purity above about 99% by weight.

13. In a process for removing olefin oxide having 2 or 3 carbon atoms from exhaust gases containing an inert diluent discharged from ethylene oxide sterilizers, the improvement comprising:

contacting said exhaust gases with an adsorbent bed capable of adsorbing an olefin oxide to provide an olefin oxide-free gas stream;

regenerating the olefin oxide from the adsorbent bed periodically to provide a more concentrated olefin oxide gas composition;

contacting said concentrated olefin oxide gas composition with an aqueous absorbing liquid at ambient pressure having an initial pH between about 0.2 and 8 and an initial temperature less than about 80 degrees F. causing absorption of at least about 97% of the olefin oxide into the aqueous liquid, said contacting being conducted at an absorbing liquid-to-gas flow rate ratio of about 40 to 500 gal/1000 ft$^3$;

feeding the aqueous liquid containing the absorbed olefin oxide at a temperature of less than about 120 degrees F. and an acid catalyst at a concentration of about 0.01 to 1 gram-mole per liter into a reactor, said reactor being at atmospheric pressure or slightly above atmospheric pressure;

reacting said aqueous liquid for a time sufficient to convert at least 97% of the olefin oxides to products including an alkylene glycol while continuously removing sufficient quantities of aqueous liquid from the reactor to keep the volume of solution in the reactor constant;

recycling the aqueous liquid leaving the reactor, after cooling, back to the absorber for further absorption of olefin oxide;

compressing the olefin oxide-free exhaust gases to a pressure of about 130 to 170 psig;

cooling the gas/liquid from the compressor to a gas/liquid temperature of about −20 to 50 degrees F.; and recovering the inert diluent having a purity above about 99% by weight.

* * * * *